United States Patent
Owman et al.

(12) 
(10) Patent No.: US 7,335,481 B2
(45) Date of Patent: Feb. 26, 2008

(54) METHODS OF IDENTIFYING COMPOUNDS THAT AFFECT A FATTY ACID CELL-SURFACE RECEPTOR

(76) Inventors: Christer Owman, Smavillsgranden 6, SE-226, 52 Lund (SE); Bjorn Olde, Vastergatan 6, SE-222, 29 Lund (SE); Knut Kotarsky, Tordmulevagen 3c, SE-227, 35 Lund (SE); Niclas Nilsson, Vlldandsvagen U:201, SE-227, 34 Lund (SE); Erik Flodgren, Ostra Vallgatan 41, SE-223, 62 Lund (SE)

( * ) Notice: Subject to any disclaimer, the term of this patent is extended or adjusted under 35 U.S.C. 154(b) by 706 days.

(21) Appl. No.: 10/202,687

(22) Filed: Jul. 24, 2002

(65) Prior Publication Data

US 2004/0019109 A1    Jan. 29, 2004

(51) Int. Cl.
    *G01N 33/53*    (2006.01)
(52) U.S. Cl. .................................. 435/7.2; 435/325
(58) Field of Classification Search ............... None
    See application file for complete search history.

(56) References Cited

U.S. PATENT DOCUMENTS 6,103,537 A * 8/2000 Ullman et al. ............... 436/526
6,365,361 B1 * 4/2002 Taniguchi et al. ........... 435/7.2
2004/0137517 A1 * 7/2004 Andrews et al. ............ 435/7.1

OTHER PUBLICATIONS

Sawzdargo, M., et al., "A cluster of four novel human G protein-coupled receptor genes occurring in close proximity to CD22 gene on chromosome 19q13.1", *Biochem. Biophys. Res. Commun.* 239:543-547 (1997).

Briscoe, C.P., et al., "The orphan G-protein-coupled receptor GPR40 is activated by Medium and Long-chain fatty acids," JBC Papers in Press, Published on Dec. 19, 2002 as Manuscript M211495200.

* cited by examiner

*Primary Examiner*—Michael Pak
(74) *Attorney, Agent, or Firm*—Finnegan, Henderson, Farabow, Garrett & Dunner, L.L.P.

(57) ABSTRACT

The present invention provides methods for screening and identifying compounds that affect the metabolism of fatty acids and fatty acid derivatives, and thus for compounds that possess anti-diabetic as well as anti-obesity properties and possess the ability to affect the levels of chylomicrons, triacylglycerols, cholesterols, and fatty acids in a patient. Kits and compositions for screening and identifying such compounds are also provided. The invention is predicated on the identification of a physiological receptor for free fatty acids and anti-diabetic and anti-obesity drugs.

12 Claims, 3 Drawing Sheets

SEQUENCE LISTING

<160> NUMBER OF SEQ ID NOS: 4

<210> SEQ ID NO 1
<211> LENGTH: 903
<212> TYPE: DNA
<213> ORGANISM: Homo sapiens

<400> SEQUENCE: 1

| | | | | | |
|---|---|---|---|---|---|
| atggacctgc | ccccgcagct | ctccttcggc | ctctatgtgg | ccgcctttgc | gctgggcttc | 60 |
| ccgctcaacg | tcctggccat | ccgaggcgcg | acggcccacg | cccggctccg | tctcacccct | 120 |
| agcctggtct | acgccctgaa | cctgggctgc | tccgacctgc | tgctgacagt | ctctctgccc | 180 |
| ctgaaggcgg | tggaggcgct | agcctccggg | gcctggcctc | tgccggcctc | gctgtgcccc | 240 |
| gtcttcgcgg | tggcccactt | cttcccactc | tatgccggcg | ggggcttcct | ggccgccctg | 300 |
| agtgcaggcc | gctacctggg | agcagccttc | cccttgggct | accaagcctt | ccggaggccg | 360 |
| tgctattcct | gggggggtgtg | cgcggccatc | tgggccctcg | tcctgtgtca | cctgggtctg | 420 |
| gtctttgggt | tggaggctcc | aggaggctgg | ctggaccaca | gcaacacctc | cctgggcatc | 480 |
| aacacaccgg | tcaacggctc | tccggtctgc | ctggaggcct | gggacccggc | ctctgccggc | 540 |
| ccggcccgct | tcagcctctc | tctcctgctc | tttttctgc | ccttggccat | cacagccttc | 600 |
| tgctacgtgg | gctgcctccg | ggcactggcc | cgctccggcc | tgacgcacag | gcggaagctg | 660 |
| cggggccgcct | gggtggccgg | cggggccctc | ctcacgctgc | tgctctgcgt | aggacccta c | 720 |
| aacgcctcca | acgtggccag | cttcctgtac | cccaatctag | gaggctcctg | gcggaagctg | 780 |
| gggctcatca | cgggtgcctg | gagtgtggtg | cttaatccgc | tggtgaccgg | ttacttggga | 840 |
| aggggtcctg | gcctgaagac | agtgtgtgcg | gcaagaacgc | aaggggcaa | gtcccagaag | 900 |

```
taa                                                              903
```

<210> SEQ ID NO 2
<211> LENGTH: 300
<212> TYPE: PRT
<213> ORGANISM: Homo sapiens

<400> SEQUENCE: 2

```
Met Asp Leu Pro Pro Gln Leu Ser Phe Gly Leu Tyr Val Ala Ala Phe
  1               5                  10                  15

Ala Leu Gly Phe Pro Leu Asn Val Leu Ala Ile Arg Gly Ala Thr Ala
             20                  25                  30

His Ala Arg Leu Arg Leu Thr Pro Ser Leu Val Tyr Ala Leu Asn Leu
         35                  40                  45

Gly Cys Ser Asp Leu Leu Leu Thr Val Ser Leu Pro Leu Lys Ala Val
     50                  55                  60

Glu Ala Leu Ala Ser Gly Ala Trp Pro Leu Pro Ala Ser Leu Cys Pro
 65                  70                  75                  80

Val Phe Ala Val Ala His Phe Phe Pro Leu Tyr Ala Gly Gly Gly Phe
                 85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
        275                 280                 285

Cys Ala Ala Arg Thr Gln Gly Gly Lys Ser Gln Lys
    290                 295                 300
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Artificial primer to amplify human GPR40/FFAR gene from human genomic DNA.

<400> SEQUENCE: 3

```
ggcggatcca ccatggacct gcccccgcag ctctccttcg                              40
```

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:  Artificial
      primer to amplify human GPR40/FFAR gene from human
      genomic DNA.

<400> SEQUENCE: 4

```
ggcggatcct tacttctggg acttgccccc ttgcgtt                                 37
```

METHODS OF IDENTIFYING COMPOUNDS THAT AFFECT A FATTY ACID CELL-SURFACE RECEPTOR

BACKGROUND OF THE INVENTION

1. Field of the Invention

The present invention relates to heptahelix receptors and methods of using them to identify compounds that have biological and pharmaceutical activity. More specifically, this invention relates to the discovery of ligands for a heptahelix receptor that was previously an unknown ("orphan") receptor, and to the development of assays to screen for other compounds that have inhibitory or activating effects on the receptor.

2. Description of Related Art

Some extracellular molecules, such as dietary substances, small molecule metabolites, hormones, vasodilators, and neurotransmitters affect the cellular activity of certain, select cells within an organism to bring about localized or systemic changes in the physiology of the organism. The effects brought about by these molecules often require interaction between the extracellular molecules and cell surface proteins present on target cells. Receptors are among the cell surface proteins that respond to these extracellular molecules, and initiate the events that lead to changes in cellular activity and, thus, physiological changes in the organism.

Cell surface receptors are membrane-spanning proteins that bind extracellular signaling molecules or otherwise sense changes in the extracellular environment, then initiate one or more signal transduction pathways to effect a cellular response. Cell surface receptors are classified based on the particular type of pathway that is induced. One of the most intensely studied classes of cell surface receptor is the class known as heptahelix receptors. These receptors bind extracellular molecules and couple that binding to binding, at the intracellular portions of the receptor, to intracellular effector proteins, such as guanine nucleotide binding regulatory proteins, which are typically referred to as G-proteins.

In general, G-protein transmembrane signaling pathways consist of three proteins: receptors, G-proteins, and effectors. As discussed above, the receptors are membrane-bound proteins that couple an external stimulus to an internal stimulus. G-proteins, which, most often, are the intermediaries in transmembrane signaling pathways of heptahelix receptors, are heterodimers that consist of alpha, beta, and gamma subunits. G-proteins transfer the signal or stimulus present on the intracellular portion of the receptor to the effectors. The effectors bring about the physiological change intended, typically through an alteration in the transcriptional activity of certain genes. Thus, in summary, signal transduction through G-protein coupled, heptahelix receptor systems proceeds as follows: 1) signal transduction is initiated by ligand (i.e., extracellular molecule) binding to a specific portion of the receptor; 2) binding of ligand causes an intracellular signal to be generated by the receptor, likely through a conformational change in the receptor; 3) the intracellular portion of the receptor binds GDP-bound G-protein, resulting in dissociation of the GDP from the G-protein; 4) the G-protein then binds GTP at the site where GDP was bound, thus activating the G-protein; 5) activated G-protein dissociates from the receptor and activates an effector protein, which regulates the intracellular levels of one or more specific second messengers; 6) hydrolysis of GTP to GDP, catalyzed by the G-protein itself, returns the G-protein to its basal, inactive form, which can bind to the receptor.

Heptahelix receptors are known to share certain structural similarities and regions of homology. For example, G-protein coupled receptors have seven hydrophobic stretches of about 20-30 amino acids each, bracketed outside the first and last and interrupted between each by at least eight hydrophilic regions of variable length. It is generally accepted that each of the seven hydrophobic regions forms an alpha helix that spans the cell membrane, and that the intervening and surrounding hydrophilic regions form alternating intracellular and extracellular loops. The seven transmembrane regions are designated TM1, TM2, TM3, TM4, TM5, TM6, and TM7. The third intracellular loop between TM5 and TM6 is believed to be the intracellular domain responsible for interaction with G-proteins. Furthermore, most receptors have single conserved cysteine residues in each of the first two extracellular loops, which form disulfide bonds that are believed to stabilize the functional protein structure. It is thought that phosphorylation and/or lipidation (e.g., palmitylation or farnesylation) of cysteine residues on some heptahelix receptors can influence signal transduction. Most heptahelix receptors contain potential phosphorylation sites within the third cytoplasmic loop and/or the carboxy terminus. The ligand binding sites of heptahelix receptors are believed to comprise a hydrophilic socket formed by several transmembrane domains surrounded by hydrophobic residues.

It is well established that many medically significant biological processes are mediated by heptahelix receptor signaling pathways. For example, the heptahelix receptor family includes dopamine receptors, which bind to neuroleptic drugs used for treating psychotic and neurological disorders, as well as receptors for calcitonin, noradrenaline, endothelin, cAMP, adenosine, acetylcholine, serotonin, histamine, thrombin, kinin, follicle stimulating hormone, opsins and rhodopsins, and odorants.

Heptahelix receptors thus play important physiological roles. Accordingly, there are many potential pharmacological uses for compounds that interact with and modulate the activity of heptahelix receptors. Indeed, a number of compounds that are known to be useful in treating various diseases in animals, including humans, are thought to exert their beneficial effects through interactions with heptahelix receptors. Examples include the blockade of β-adrenergic receptors in cardiac disease, the blockade of serotonin receptors in migraine, the blockade of leukotriene receptors in inflammatory diseases, and the blockade of purine receptors to exert thrombolytic effects. In fact, most of the drugs now in clinical use exert their effects by interfering, in some fashion, with heptahelix receptors.

Unfortunately, an understanding of the pharmacology of compounds that interact with heptahelix receptors, and the ability to rapidly identify compounds that specifically interact with them to provide desired therapeutic effects, have been hampered by the lack of rapid and sensitive methods or assays to identify those compounds. In vitro methods are commonly used now to screen and identify candidate compounds. For example, a rapid, sensitive method for identifying ligands for heptahelix receptors was recently developed (Kotarsky et al., 2001). The availability of this method has enabled researchers to screen a large number of compounds to identify those that show promise as pharmaceuticals, or at least to identify core compounds that can be modified to yield pharmaceuticals.

Lipids are small molecules that can be found both intracellularly and extracellularly in animals, including humans. Lipids provide energy to the cell and contribute to cellular components including organelles and the plasma membrane.

Thus, they serve a role in both the metabolism of cells and in the physical structure of cells.

The simplest lipids are the fatty acids. Fatty acids are long chain hydrocarbons attached to carboxyl groups. They are classified generally in two categories—saturated and unsaturated. Saturated fatty acids derive their name from the fact that every carbon atom in their chains is fully saturated (i.g., each internal carbon is bound to two hydrogen atoms and the terminal non-carboxyl carbon is part of a methyl group). Accordingly, all the bonds between the carbons in the chain are single bonds. In contrast, unsaturated fatty acids contain carbons that are not saturated with hydrogens—they contain carbon-carbon double bonds. Naturally occurring unsaturated fatty acids contain double bonds that are in the cis configuration, whereas artificially produced unsaturated fatty acids contain double bonds that are in the trans configuration. Trans fatty acids are found in margarine and other foods, and have been linked with heart disease. The most common saturated fatty acids in humans are palmitic acid ($C_{16}$) and stearic acid ($C_{18}$). The most common unsaturated fatty acid in humans is oleic acid ($C_{18}$).

Fatty acids serve as the building blocks for various higher lipids, such as triglycerides (triacyl glycerols), phospholipids, steroids (such as cholesterol), and lipoproteins (such as chylomicrons, the very low density lipoproteins (VLDLs), the low density lipoproteins (LDLs), and the high density lipoproteins (HDLs)). Diabetics typically have elevated chylomicron and VLDL levels and depressed levels of LDLs, whereas people with high cholesterol diets typically have elevated LDL and VLDL levels. Persons with gout typically have elevated LDL and VLDL levels. Alcoholics typically have elevated chylomicron, LDL, and VLDL levels. Furthermore, elevated trans fatty acids in a diet have been shown to be linked to hypercholesterolemia, atherosclerosis, coronary artery disease, and coronary heart disease. Thus, although essential nutritional components, fatty acids are known risk factors in cardiovascular and metabolic diseases. (See, for example, Unger, 2002.)

During the last decade, it has become evident that different classes of lipids serve as chemical messengers in the body. (Chawla et al., 2001.) For example, the eicosanoids prostaglandin and leukotriene, which are derived from the fatty acid arachidonic acid ($C_{20}$), are now known to act as extracellular signaling molecules in vasodilation, muscle contraction, and chemotaxis, and are involved in allergy and anaphylaxis. Likewise, oleic acid has recently been shown to be involved in triggering neutrophil aggregation and neutrophil adherence to epithelial cells, and has thus been implicated in fat embolisms that cause acute respiratory distress. (Mastrangelo et al., 1998.) Interestingly, oleic acid has also been linked to the low incidence of atherosclerotic disease in Mediterranean countries, where intake of oleic acid is relatively high. The effect of oleic acid appears to take place through modulation of expression of endothelial leukocyte adhesion molecules. (See, for example, Massaro et al., 1999.) The nutritional and metabolic effects of short-chain fatty acids have been well described. (Linder, 1991).

It is now clear that lipids play an essential and important role as both dietary components and disease factors. Accordingly, there is a need in the art to identify mechanisms by which lipids and more complex molecules derived from them are metabolized or exert their specific effects on diseases or disorders. By identifying and understanding the mechanisms of lipid metabolism and lipid interaction with various diseases and disorders, new drugs and treatment regimens for the diseases and disorders can be developed and delivered to those suffering from, or at risk of developing, the diseases or disorders.

SUMMARY OF THE INVENTION

The present invention addresses the need in the art for a better understanding of the messenger role of dietary fatty acids, and thus the need for new drugs to treat diseases and disorders associated with the cellular effects of fatty acids. The invention addresses this need by identifying the activity of a heptahelix receptor previously lacking a known function. As a result of this identification, the invention provides a screening assay for compounds that affect the activity of the receptor.

In general, the invention provides for the use of the GPR40 receptor to identify compounds that have physiological function. The compounds to be identified have a general structure comprising i) a hydrophobic region having a length equivalent to 10-18 carbon-carbon bonds and ii) a hydrophilic group on one or both ends of the hydrophobic region. The compounds are contemplated to have clinical and pharmaceutical relevance, as, for example, drugs for treating diseases and disorders involving fatty acid or fatty acid derivative metabolism, such as atherosclerosis, diabetes, and obesity. Most conveniently, the invention is practiced in vitro, that is, by using cells grown in laboratory media under defined conditions, or in cell-free compositions.

Heptahelix receptors can be solubilized, reconstituted, and displayed in a cell-free form, either as detergent-solubilized entities or they can be reconstituted into a phospholipid bilayer covering a solid support, e.g., paramagnetic beads. Receptor-loaded magnetic beads can be used to select for substances specifically binding to the receptor in a similar way as in cells expressing the recombinant receptor.

In one aspect, the invention provides a method of screening for one or more compound that affects the cellular function of fatty acids or fatty acid derivatives. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway. The method can also include identification of one or more compounds showing a desired level of activity.

In another aspect, the invention provides a method of screening for one or more compounds that affect the binding of fatty acids or fatty acid derivatives by cells expressing the receptor of the invention. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway. The method can also include identification of one or more compounds showing a desired level of activity.

In yet another aspect, the invention provides a method of screening for one or more compounds that possess anti-diabetic or anti-obesity properties. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway. The method can also include identification of one or more compounds showing a desired level of anti-diabetic activity.

In a further aspect, the invention provides a method of screening for one or more compounds that affect the levels of chylomicrons, triacylglycerols, cholesterols, and fatty acids or combinations of two or more of these, in a subject. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway. The method can also include identification of one or more compounds showing a desired level of activity.

In yet a further aspect, the invention provides kits for performing one or more of the methods of the invention. The kits can comprise some or all of the reagents, materials, and instructions necessary for performing the methods of the invention. Accordingly, the invention provides for use of such kits.

Another aspect of the invention is a composition that comprises an isolated or purified GPR40 protein bound to a fatty acid or fatty acid derivative.

Additional aspects and advantages of the invention will be set forth in part in the description that follows, and in part will be derived from the description, or can be learned by practice of the invention. The various aspects, embodiments, and advantages of the invention can be realized and attained through the steps, elements, and/or combinations particularly pointed out in the appended claims. It is to be understood that both the foregoing general description and the following detailed description are exemplary and explanatory only, and are not to be considered a restriction on the invention, as claimed.

BRIEF DESCRIPTION OF THE DRAWINGS

The accompanying drawings, which are incorporated in and constitute a part of this specification, illustrate aspects and/or embodiments of the invention, and together with the written description, serve to explain the principles of the invention.

A. CHO cells transfected with FFAR (R10; GPR40);
  B. Sham-transfected CHO cells;
  C. HeLa cells transfected with FFAR (R10; GPR40); and
  D. Sham-transfected HeLa cells.
The LA concentrations are the same in all four panels.

The relative responses shown in FIG. 3 were adjusted to the same relative level as used in FIG. 1.

DETAILED DESCRIPTION OF THE INVENTION

This invention provides for the first time that a cell surface heptahelix receptor, which we name FFAR (for Free Fatty Acid Receptor), is activated by free fatty acids having more than eight but fewer than twenty carbon atoms. This receptor belongs to the class of seven transmembrane heptahelix receptors (GPCRs) and responds to free fatty acids comprising 10 to 18 carbon atoms. It is notable that the receptor also mediates responses to anti-diabetic drugs belonging to the group of thiazolidinediones. The receptor also mediates responses to the experimental anti-obesity drug, MEDICA 16. FFAR is expressed in skeletal muscle, heart, liver, and pancreatic beta cells. In view of the nature of the activating substances and the tissue distribution the term "nutrient sensor" is used for receptors acting at the interface between dietary components and signaling molecules.

The putative heptahelix receptor GPR40 was recognized during a search for human galanin receptor subtypes. (Sawzdargo et al., 1997.) The gene encoding the GPR40 protein (SEQ ID NO:1) is located downstream of the CD22 gene. The deduced GPR40 protein (SEQ ID NO:2) is 300 amino acids in length and shows highest identity with heptahelix receptor family members GPR43 (28% identity), IL-8AR (26% identity), P2Y6 (25% identity), and ThrbRP (23% identity). The GenBank accession number for the GPR40 sequence is reported as AF024687. However, Sawzdargo et al. discloses no function for the putative GPR40 protein.

According to the present invention, FFAR includes not only the protein specifically consisting of the amino acid sequence of SEQ ID NO:2, but variants of it that have essentially the same biological function and ligand binding profile as the protein produced from SEQ ID NO:2. Thus, FFAR includes mutants and derivatives (i.e., proteins that are post-translationally modified) of SEQ ID NO:2 that do not alter the essential biological function and ligand binding profile of the protein produced from SEQ ID NO:2. Likewise, nucleic acids encoding FFAR are not limited to those comprising SEQ ID NO:1. Rather, nucleic acids encoding FFAR include nucleic acids that encode proteins that have essentially the same biological function and ligand binding profile as the protein produced from SEQ ID NO:2.

In one aspect, the invention provides a method of screening for one or more compounds that affect the function of fatty acids or fatty acid derivatives. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway. The method can also include identification of one or more compounds showing a desired level of activity.

The method can comprise providing a cell expressing FFAR, exposing the cell to one or more compounds under conditions where the compounds can contact the FFAR, and determining whether the activity of the FFAR has been affected.

By compound, it is meant any chemical entity that binds to, activates, or inhibits the receptor. Such an entity can have a general structure comprising i) a hydrophobic region having a length equivalent to 10-18 carbon-carbon bonds and ii) a hydrophilic group on one or both ends of the hydrophobic region. Exemplary compounds include, but are not limited to, fatty acids and compounds derived from fatty acids. Particular compounds exemplified below are fatty acids and other compounds having structural or functional similarities to fatty acids (i.e., fatty acid derivatives). Compounds that are derived from fatty acids are compounds that can be synthesized, either biologically or chemically, using a fatty acid as a starting material. Thus, fatty acid derivatives include compounds that are created through a single step or multiple steps, using one or more fatty acids as a starting material. Accordingly, a fatty acid derivative can be larger and/or more complex than the starting fatty acid, or it can be smaller and/or less complex than the starting fatty acid. It is to be understood that, in creating a fatty acid derivative, such as by combinatorial chemistry, it is not necessary to physically include a fatty acid in the synthesis scheme. Rather, it is sufficient to design the compound using the structure of a fatty acid, or the structure of a compound known to be a metabolic precursor or product of a fatty acid, as a guide.

The compounds contemplated by the present invention have a central hydrophobic region that has a length that is approximately the length of 10-18 linear carbon-carbon bonds. However, the compounds are not limited only to $C_{10-18}$ alkyl or alkenyl compounds. Rather, it is the length of the hydrophobic region that serves as the basis for determining whether a compound is contemplated by the invention. Accordingly, compounds that contain bonds in the hydrophobic region other than linear carbon-carbon bonds are contemplated by the present invention. For example, compounds that contain carbon-oxygen-carbon bonds within the hydrophobic region are contemplated, as are compounds that contain carbon-nitrogen-carbon bonds, or other types of bonds. Accordingly, the presence of an atom that might impart some hydrophilic character to the hydrophobic region does not exclude the compound from within those contemplated by the invention. It is the hydrophobic character of the entire region (i.e., excluding the hydrophilic head and/or tail of the compound) that is to be considered.

Likewise, the presence of one or more non-linear bond (e.g., cyclic groups) within the hydrophobic region is contemplated for compounds of the invention. When a non-linear bond is present, the total length of the hydrophobic region can be calculated by counting the number of chemical bonds required to traverse the non-linear group, from where the linear chain (or hydrophilic head/tail) joins the non-linear group at one atom of the non-linear group, to where the linear chain continues from the non-linear group. Indeed, the compound may comprise multiple ring structures fused together.

It is to be understood that the compounds contemplated by the invention may have any type of substitution on the linear chain comprising the hydrophobic region, so long as the substitution retains the hydrophobic character of the hydrophobic region.

Specifically, the compounds contemplated by the present invention can have a hydrophobic region having a length of 10 bonds, 12 bonds, 14 bonds, 16 bonds, or 18 bonds. The bonds can be of any type, including single bonds, double bonds, and triple bonds. One hydrophobic region can contain a single type of bond or mixtures of two or more types of bonds. For example, where the compound is a fatty acid, it can be a saturated fatty acid, an unsaturated fatty acid, or a polyunsaturated fatty acid. Likewise, where there is a restriction on the rotation about one or more bonds, any configuration (e.g., cis or trans) is acceptable. Of course, because chemical bonds stretch and contract depending on various physical conditions, the length of the hydrophobic region will expand and contract somewhat, depending on the conditions under which it is found. Thus, the lengths described herein are to be understood as approximate, and to include variations due to stretching and contracting of the bonds between one, some, or all of the atoms comprising the hydrophobic region.

Exemplary compounds include, but are not limited to, capric acid, lauric acid, myristic acid, palmitic acid, oleic acid, linoleic acid, linolenic acid, γ-linolenic acid, stearidonic acid, Ciglitazone ((±)-5-[4-(1-methylcyclohexylmethoxy)-benzyl]thiazolidine-2,4-dione), CLA (trans-10, cis-12-octadecanoic acid), 9-HODE (9-hydroxy,trans-10, cis-12-octadecanoic acid), EDA (cis-11 ,cis-14-eicosadienoic acid), ricinoleic acid, ricinelaidic acid, elaidic acid, hydroxystearic acid, palmitoleic acid, and myristelaidic acid.

In practicing the invention, the compound can be used in any form, including, but not limited to, a purified form, a partially purified form, as the sole solute in a solution, as one of two or more solutes in a solution, as a component of a dispersion or colloidal composition, and/or as a component in a complex mixture of solids, liquids, and/or gases.

Any cell or artificial cell-free system expressing the FFAR can be used. The requirement for an artificial, non-cellular system is that the compound binds specifically to the FFAR receptor protein. The requirement for a cell is to provide a mechanism for detecting interaction of the molecule(s) being screened with FFAR. Thus, a cell that naturally expresses FFAR can be used, as long as FFAR activity is linked to some means for detecting a change in FFAR activity. The requirement for an artificial cell-free system is that the molecule(s) being screened bind specifically to FFAR. In preferred embodiments, recombinant cells are used. By recombinant cell, it is meant a cell that expresses, either transiently or stably, at least one nucleic acid sequence that has been introduced into the cell through human-directed activities. Thus, recombinant cells include cells that have been engineered through recombinant nucleic acid technology and through genetic recombination, as well as those created using other laboratory techniques known to those of skill in the art. In preferred embodiments, recombinant cells that are suitable for high throughput screening are used.

Many recombinant and non-recombinant cells and assay systems for detecting activity of heptahelix receptors are known in the art. Any of these cells and systems can be used to screen for compounds that affect the activity of FFAR. Suitable systems include those in which activation of a heptahelix receptor is linked, via a natural or recombinantly constructed intracellular signal transduction pathway, to expression of one or more reporter genes whose products can be detected or can produce a detectable signal. A preferred system is that disclosed in Kotarsky et al., 2001, in co-pending U.S. application Ser. No. 09/946,334, filed Sep. 21, 2001, and in the references cited in therein. The entire disclosure of application Ser. No. 09/946,334 is relied upon and incorporated by reference herein. Other suitable systems include, but are not limited to, those based on the systems disclosed in U.S. Pat. No. 5,401,629 to Harpold et al., in U.S. Pat. No. 5,436,128 to Harpold et al., and in U.S. Pat. No. 5,854,004 to Czernilofsky et al.

As used herein, gene means any amount of nucleic acid material that is sufficient to encode a protein having the function desired. Thus, it includes, but is not limited to, genomic DNA, cDNA, RNA, and nucleic acid that is otherwise genetically engineered to achieve a desired level of expression under desired conditions. Accordingly, it includes fusion genes (encoding fusion proteins), intact genomic genes, and DNA sequences fused to heterologous promoters, operators, enhancers, and/or other transcription regulating sequences. Methods and nucleic acid constructs for preparing genes for recombinant expression are well known and widely used by those of skill in the art, and thus need not be detailed here.

In a preferred embodiment, the method of screening for at least one compound that affects metabolism of at least one fatty acid comprises: a) providing a cell that expresses FFAR on its cell surface, and that comprises an intracellular signal transduction pathway that couples activation of FFAR to expression of one or more reporter genes; b) contacting the cell with one or more compounds under conditions were interaction of a compound with FFAR can cause expression of one or more reporter genes through one or more intracellular signal transduction pathways; and c) determining whether one or more of the reporter genes was expressed by detecting expression of one or more of the reporter gene.

Determining (or detecting) expression of a reporter gene can be through detection of mRNA expressed from a reporter gene, detection of a protein encoded by a reporter gene, or detection of a signal produced as a result of the activity of a protein expressed by a reporter gene. Methods for detecting mRNA are well known to those of skill in the art, and thus need not be detailed here. Likewise, any known protein can be used as a reporter protein. Methods for detecting proteins (including, but not limited to, immunological techniques and activity assays) are well known to those of skill in the art, and thus need not be detailed here. Preferred proteins to be used as reporter proteins are those that provide, either intrinsically or through their biochemical activity, a signal that can be detected directly. For example, enzymes that produce color changes or light, and proteins that are intrinsically luminescent, are preferred. Examples include, but are not limited to, firefly luciferase, *Renilla* luciferase, vargula luciferase, green fluorescent protein, enhanced green fluorescent protein, aequorin, secreted alkaline phosphatase, and β-galactosidase.

Where appropriate or desired, control assays can be conducted to determine the level of detectable signal produced by the system in the absence of the compound of interest, in the absence of FFAR, in the absence of one or more reporter genes, or in the absence of one or more members of the signal transduction pathway being used to link the activity of FFAR to expression of the reporter gene.

The method can be performed on any suitable scale. For example, it can be performed by exposing a cell, or culture of cells, to a single compound at a time. Likewise, it can be performed using high-throughput screening techniques to screen thousands of compounds at a time.

The method can also include identification of one or more compounds showing a desired level of activity. That is, the method can further comprise selecting one or more compounds, or one or more samples containing one or more compound, to determine the chemical identity (e.g., structure) of the compounds or compounds affecting the activity of the FFAR. In assays where the identity of each compound being tested is known before performing the assay, identifying the compound might simply be a matter of confirming one or more physical or biochemical properties of the molecule. In assays where more than one compound per cell is tested at a time (i.e., one cell is exposed to more than one compound), identifying the compound might include separating the individual compounds from each other, then performing the assay again, with a single compound being exposed to a single cell or cell culture. Techniques for identifying compounds are known to those of skill in the art, and thus do not need to be detailed here. Exemplary techniques include, but are not limited to spectroscopy, such as mass spectroscopy and X-ray diffraction spectroscopy, IR, NMR, and chromatography, chemical degradation and/or characterization, and crystallography.

The compounds identified through the screening method can either activate or repress the activity of FFAR. Accordingly, the compounds can activate or inhibit fatty acid function of cells expressing FFAR and/or the function of compounds derived from one or more fatty acids. While the present invention is not limited to any particular mechanism of action, this invention contemplates that certain molecules will act as substitutes for the physiological ligands of FFAR (i.e., as fatty acid and lipid mimics). The activity of these molecules mediated by FFAR can alter many functions of the cell expressing FFAR including, but not limited to, altered fatty acid metabolism. These molecules can cause cells expressing FFAR to activate fatty acid and/or fatty acid derivative metabolism pathways, reducing the amount of fatty acids and fatty acid derivatives, such as lipids, being released by these cells. Depending on the basal level of metabolism of fatty acids and lipids in a given patient, the effects of these compounds include 1) reduction or elimination of the improper production and secretion (i.e., anabolic production) of certain fatty acid(s) or fatty acid based compounds, such as cholesterol and lipoproteins, or 2) enhancement of the production and secretion of certain fatty acids or fatty acid based compounds. Accordingly, the various compounds identified by the methods of the invention can be used to either activate or repress fatty acid and/or fatty acid derivative metabolism, as well as other cell functions mediated by FFAR.

On the other hand, this invention also contemplates that certain compounds inhibit fatty acid metabolism and other cell functions coupled to FFAR by binding to FFAR in an unproductive manner. The net effect of this binding is to occupy FFAR molecules that would otherwise be bound by fatty acids and/or their derivatives, resulting in repression of fatty acid and/or fatty acid derivative metabolic pathways on other cellular functions that would be activated in the absence of the compound. Depending on the basal level of metabolism of fatty acids and their derivatives in a given patient, the effects of these compounds could be to either 1) reduce or eliminate the improper hyperactivation of genes involved in cell functions regulated by FFAR including, but not limited to, production (i.e., anabolic production) and secretion of certain fatty acids or fatty acid derivatives, such as cholesterol and lipoproteins, or 2) enhance cell functions, including the production and secretion of certain fatty acids or fatty acid derivatives whose expression is improperly inhibited in the affected cell by hyperactivation of the FFAR or a member of the signal transduction pathway linked to FFAR. Accordingly, the various compounds identified by the methods of the invention can be used to activate or repress various cell functions mediated by FFAR.

By "patient" it is meant any living animal, including, but not limited to, a human, who has, or is suspected of having or being susceptible to, a disease or disorder, or who otherwise would be a subject of investigation relevant to fatty acid metabolism disorders or disorders related to fatty acid derivatives. Accordingly, a patient can be an animal that has been bred or engineered as a model for heart disease, artery disease, obesity, diabetes, or any other disease or disorder. Likewise, it can be a human suffering from, or at a high risk of developing, a disease or disorder associated with fatty acid or fatty acid derivative metabolism. Similarly, a patient can be an animal, including a human, who is serving as a healthy control for investigations into diseases and/or disorders associated with fatty acid and/or fatty acid derivative metabolism.

In another aspect, the invention provides a method of screening for one or more compounds affecting binding and/or uptake of fatty acids or fatty acid derivatives by cells expressing FFAR. The screening method generally comprises a) contacting a cell expressing the receptor of the invention with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter linked to the receptor through a signaling pathway.

The method can comprise providing a cell or an artificial support expressing FFAR, exposing the expression system to one or more compounds under conditions where the compounds can contact the FFAR, and determining whether the binding and/or activity of the FFAR has been affected.

The compounds, cells, reporter molecules, and assay systems can be those described above with regard to the method of screening for compounds that affect cell function, including fatty acid metabolism.

In a preferred embodiment, the method of screening for at least one compound that affects binding and/or uptake of fatty acids comprises: a) providing a "cell" that expresses FFAR on its surface, and that comprises an intracellular signal transduction pathway that couples activation of FFAR to expression of one or more reporter genes; b) contacting the cell with one or more compounds under conditions were interaction of a compound with FFAR can cause expression of one or more reporter genes through one or more intracellular signal transduction pathways; and c) determining whether one or more reporter genes was expressed by detecting expression of one or more of the reporter gene. Binding is measured in assays well-known to the art.

Where appropriate or desired, control assays can be conducted to determine the level of detectable signal produced by the system in the absence of the compound of interest, in the absence of FFAR, in the absence of one or more reporter genes, or in the absence of one or more members of the signal transduction pathway being used to link the activity of FFAR to expression of the reporter gene.

The method can also include identification of one or more compounds showing a desired level of activity. That is, the method can further comprise selecting one or more compounds, or one or more samples containing one or more compounds, to determine the chemical identify (e.g., structure) of the compound or compounds that is/are affecting the activity of FFAR. In assays where the identity of each compound being tested is known before performing the assay, identifying the compound might simply be a matter of confirming one or more physical or biochemical property of the molecule. In assays where more than one compound per cell is tested at a time (i.e., one cell is exposed to more than one compound), identifying the compound might include separating the individual compounds from each other, then performing the assay again, with a single compound being exposed to a single cell or cell culture. Techniques for identifying compounds are known by those of skill in the art, as discussed above.

In yet another aspect, the invention provides a method of screening,for one or more compounds that possesses anti-diabetic or anti-obesity properties. The screening method generally comprises a) contacting a cell expressing FFAR with one or more compounds that specifically interact with FFAR, and having a general structure comprising, but not limited to, i) a hydrophobic region having a length equivalent to 10-18 carbon-carbon bonds and ii) a hydrophilic group on one or both ends of the hydrophobic region, and b) determining whether the cell function is affected by, for example, expression of a reporter gene linked to the receptor through a signaling pathway.

The method can comprise providing a cell expressing FFAR, exposing the cell to one or more compounds under conditions where the compound(s) can contact the FFAR, and determining whether the activity of the FFAR has been affected.

Here again, the compounds, cells, reporter genes, and assay systems can be those described above with regard to the method of screening for compounds that affect cell function, including fatty acid metabolism.

In a preferred embodiment, the method of screening for at least one compound that possesses anti-diabetic or anti-obesity properties comprises: a) providing a cell that expresses FFAR on its cell surface, and that comprises an intracellular signal transduction pathway that couples activation of FFAR to expression of one or more reporter genes; b) contacting the cell with one or more compounds under conditions in which interaction of a compound with FFAR can cause expression of one or more reporter molecules through one or more intracellular signal transduction pathways; and c) determining whether one or more reporter genes was expressed by detecting expression of one or more reporter molecules.

Once again, where appropriate or desired, control assays can be conducted to determine the level of detectable signal produced by the system in the absence of the compound of interest, in the absence of FFAR, in the absence of one or more reporter genes, or in the absence of one or more members of the signal transduction pathway being used to link the activity of FFAR to expression of the reporter gene.

The method can further include testing the one or more compounds having activity with respect to the FFAR for anti-diabetic or anti-obesity properties. Suitable systems for determining the effect of compounds on diabetes and obesity are known in the art. Any suitable system can be used, such as measurement of glucose uptake or insulin secretion.

In a further aspect, the invention provides a method of screening for one or more compounds that affect the levels of chylomicrons, triacylglycerols, cholesterols, fatty acids, or combinations of two or more of these, in a patient. The screening method generally comprises a) contacting a cell expressing FFAR with one or more compounds having a general structure comprising i) a hydrophobic region having a length equivalent to 10-18 carbon-carbon bonds and ii) a hydrophilic group on one or both ends of the hydrophobic region, and b) determining whether the cell function is affected by, for example, expression of a reporter molecule linked to the receptor through a signaling pathway. The method can comprise providing a cell expressing FFAR, exposing the cell to one or more compounds under conditions where the compounds can contact the FFAR, and determining whether the activity of the FFAR has been affected. The compounds, cells, reporter genes, and assay systems can be those described above with regard to the method of screening for compounds that affect fatty acid metabolism.

In a preferred embodiment, the method of screening for at least one compound that affects the levels of chylomicrons, triacylglycerols, cholesterols, and fatty acids or combinations of two or more of these, in a patient comprises: a) providing a cell that expresses FFAR on its cell surface, and that comprises an intracellular signal transduction pathway that couples activation of FFAR to expression of one or more reporter genes; b) contacting the cell with one or more compounds under conditions where interaction of a compound with FFAR can cause expression of one or more reporter genes through one or more intracellular signal transduction pathways; and c) determining whether one or more reporter genes was expressed by detecting expression of one or more reporter gene.

The method can further include testing the one or more compounds having activity with respect to the FFAR for ability to affect the level of chylomicrons, triacylglycerols, cholesterols, fatty acids, or combinations of two or more of these, in a patient. Suitable systems for determining the effect of compounds on the levels of these fatty acid derivatives are known the art. Any suitable system can be used. The nutritional and metabolic effects of short-chain fatty acids have been well described. (Linder, 1991.)

In yet a further aspect, the invention provides kits for performing one or more of the methods of the invention. The kits can comprise some or all of the reagents, materials, and instructions necessary for performing the methods of the invention. The reagents and materials can be included in separate containers or combinations of reagents and materials can be combined in one or more container within the kit.

By reagents, it is meant any element, molecule, or compound that is present in the assay system and participates, either directly or indirectly, in the biochemical processes occurring during performance of the method. Reagents thus include, but are not limited to, nucleic acids, cells, media, compounds used for introducing nucleic acids into cells, compounds used to generate detectable signals, etc.

By materials, it is meant items that are used to contain and/or perform the methods of the invention, but that do not participate in any of the biochemical reactions taking place in the method. Materials thus include, but are not limited to, containers, culture dishes, spatulas or other devices for distributing reagents, devices for electrically or electrochemically introducing nucleic acids into cells, devices for detecting signals produced by signal generating proteins, etc.

Instructions for performing the methods of the invention can be provided in any suitable form, such as on a sheet of paper, a placard, or a booklet. Likewise, the instructions may be printed on the package containing the kit, or on one or more of the containers that might be provided to contain various reagents.

In one embodiment, the kit comprises a nucleic acid comprising a gene encoding FFAR. The nucleic acid is preferably one that can be incorporated, either transiently or stably, into a host cell, and that can be expressed to produce a functional FFAR within the host cell (which, upon insertion of the nucleic acid, becomes a recombinant cell). The nucleic acid thus can be in any suitable form, including, but not limited to, naked, linear or circular nucleic acid (such as genomic DNA, mRNA, cDNA, plasmid DNA, cosmid DNA, phagemid DNA, or viral nucleic acid), viral nucleic acid present in an intact virus, nucleic acid encapsulated by liposomes or other delivery molecules, etc. Alternatively, the nucleic acid can be provided as a component of a recombinant cell, either as a transient component (e.g., a plasmid within the cell) or as a stable component (e.g., incorporated into the host cell's genome).

In another embodiment, the kit comprises the FFAR protein expressed by a host cell suitable for the introduction of a nucleic acid encoding FFAR. In yet another embodiment, the kit comprises a recombinant cell, i.e. one that comprises at least one heterologous gene. The recombinant cell can comprise a) a heterologous gene encoding FFAR, b) one or more heterologous genes encoding members of a signal transduction pathway that link FFAR to expression of a reporter gene, c) one or more reporter genes, or d) a combination of one or more of these. A kit can comprise a host cell, a recombinant cell, or both.

In a further embodiment, the kit comprises the FFAR protein in a cell-free milieu. The milieu can comprise FFAR protein that is solubilized, reconstituted, and displayed in a cell-free form, or it can be reconstituted into a phospholipid bilayer covering a solid support, e.g., a paramagnetic bead. The kit can comprise proteinaceous members of a signal transduction pathway that links FFAR to expression of a reporter molecule, one or more reporter molecules, or a combination of one or more of these.

The kits of the invention preferably comprise at least one fatty acid or fatty acid derivative that is known to bind and activate FFAR. The fatty acid or fatty acid derivative can be used as a control to ensure that the method of the invention has been performed as expected. Suitable fatty acids are those having a hydrophobic chain length of from 10 to 18 carbons in length.

Another aspect of the invention is a composition that comprises an isolated or purified FFAR bound to a fatty acid or fatty acid derivative. Such compositions are generally produced as a result of performing the methods of the present invention or using the kits of the present invention. However, specific compositions comprising isolated or purified FFAR bound to a fatty acid or fatty acid derivative can also be made for other reasons. For example, such a composition can be made in order to perform competitive assays. For example, a competitive assay can be performed to determine whether a compound can displace the pre-bound fatty acid from the FFAR, providing information on relative binding efficiencies and strengths for various compounds that bind to FFAR. Other uses for compositions comprising FFAR bound to a fatty acid or fatty acid derivatives are apparent to those of skill in the protein biochemistry and pharmaceutical arts, and thus need not be detailed here.

EXAMPLES

Free fatty acids (FFAs), particularly poly-unsaturated free fatty acids, appear in a plethora of studies focusing on their metabolic function in all types of cells and tissues. Over the last few years, it has been noted that some FFAs also have a messenger role (Nunez, 1997), mediated via the nuclear peroxisomal proliferator-activated receptors (PPAR) (Berger and Moller, 2002). However, all biological effects reported cannot be explained by these mechanisms. Some of the mediator effects appear to be PPAR independent (Sauer et al. 2000; Brunmair et al., 2001; Louet et al., 2001), instead displaying characteristics of cell surface receptor involvement. Among FFAs, so far only arachidonic acid (AA) has been found to constitute a precursor of signaling molecules, acting through surface receptors, notably heptahelix receptors. (Funk, 2001.) Linoleic acid (LA) is one of several medium- to long-chain essential fatty acids forming the starting point in liponeogenesis and fatty acid metabolism, including the formation of, among other things, AA and its metabolites (Samuelsson et al., 1985). In addition, they are key components in dietary fat and particularly abundant in plant oils and fish. (Linder, 1991.)

Taken together, this prompted an investigation of these FFAs using a screening approach aimed at identifying potential surface receptors. We used a highly sensitive reporter system (Kotarsky et al., 2001) expressing each of ten different putative human heptahelix receptors, for which the endogenous activating ligands were still unknown (i.e., "orphan receptors"), was used. The receptor sequences were selected from GenBank, based on a reasonably high sequence homology to the receptors for leukotriene $B_4$ (an AA derivative), previously cloned. (Owman et al., 1996; Tryselius et al., 2000.)

The following Examples report, in detail, the screening and identification of the receptor and its physiological function. The Examples, which are intended to be purely exemplary of the invention, and should therefore not be considered to limit the invention in any way, also describe and detail aspects and embodiments of the invention discussed above.

Example 1

Materials and Methods

Cloning

Cloning of the R10/GPR40 ORF from human genomic DNA was performed by PCR using the following primers.

```
forward: 5'-GGCGGATCCACCATGGACCTGCCCCCGCAGCTCTCCTTCG-3';  (SEQ ID NO:3)

reverse: 5'-GGCGGATCCTTACTTCTGGGACTTGCCCCCTTGCGTT-3'.  (SEQ ID NO:4)
```

PCR conditions were: 96 degrees C. for 3 min, 96 degrees C. for 45 sec; 57 degrees C. for 1 min; and 72 degrees C. for 1 min (30 cycles). The PCR product was restricted with BamHI, subcloned into the pIRESpuro vector (Clontech), and sequenced.

Cell Culture

HeLa, CHO, and MIN-6 cells were grown in Dulbecco's Modified Eagle's medium with Glutamax-I supplemented with 10% FBS, 0.5% streptomycin and penicillin at 37 degrees C. with 7% $CO_2$, and split twice a week to the ratio of 1:10.

HFF11 Reporter Cells and Assay

Construction of the HFF11 reporter cell lines (successor of the previously described HeLa based cell line, HF1) expressing the orphan GPCRs studied was performed as earlier reported. (Co-pending U.S. application Ser. No. 09/946,334 filed Sep. 21, 2001; Kotarsky et al. 2001.) They contain the reporter plasmid, pcFUS3, where the original promoter region has been extended by 6 NFkB and 6 STAT elements. (Co-pending U.S. application Ser. No. 09/946,334 filed Sep. 21, 2001; Kotarsky et al., unpublished.) On day 1, HFF11 reporter cells, with or without the test heptahelix receptor, were seeded into 96-well plates at 20,000 cells per well in 100 μl growth medium. On day 3, the medium was removed and replaced by 90 μl serum-free medium. Substances (e.g., compounds) and controls were added in the appropriate concentrations 24 h later. Stimulations were performed at 37 degrees C. for 7 h. Cell lysates were assayed in a BMG Lumistar Galaxy luminometer as previously described. (Kotarsky et al., 2001.)

Aequorin Reporter Assay

Cells were seeded the day before transfection in a 6-well plate (400,000 cells/well). Then, 0.8 μg of PCDM.AEQ reporter plasmid (Button et al., 1993.) and 1 μg pIRE-Spuro.R10 receptor plasmid, or pcEGFP for controls, were mixed with 100 μl OptiMEM containing 5 μl per transfection of PLUS reagent. After 15 min., 100 μl OptiMEM and 9 μl (HeLa cells) or 6 μl (CHO cells) of lipofectamine were added and incubated for another 15 min. Then, 800 μl OptiMEM were added, and the cells were washed and incubated with the transfection solution for 5 h. Two days after transfection, cells were loaded with 10 μM coelenterazine and injected into a 96-well plate containing test or control (vehicle) substances. Light emission was recorded for 1 min in a BMG Lumistar Galaxy luminometer and normalized to total emission using 0.1% and 100 mM $CaCl_2$ for each well.

Northern Blot

Two μg mRNA prepared from MIN-6 cells was electrophoresed, together with a RNA size marker, and transferred to a nylon membrane according to standard procedures. (See, for example, Ausubel, 1989.) The membrane and a pre-made human multiple tissue Northern blot was hybridized with the cloned R10/GPR40 ORF according to standard (50% DMF at 42 degrees C.) protocols (e.g., Ausubel, 1989) and subjected to autoradiography.

Data Analysis

Statistical analysis of the drug concentration-response data was carried out with the GraphPad PRISM software package.

Example 2

Identification and Characterization of FFAR FFA Binding and Tissue Distribution

Figure 1:
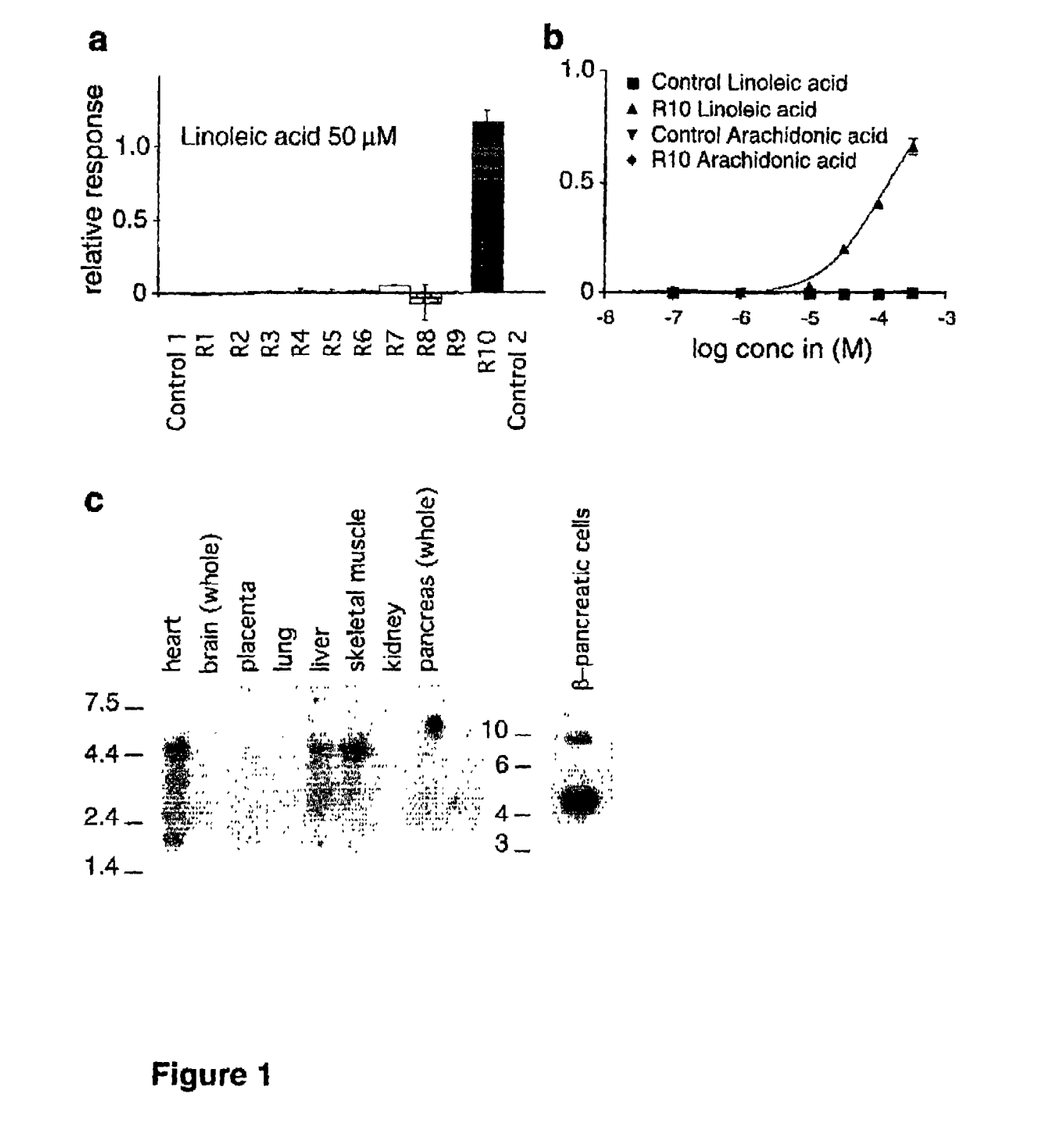
FIG. 1 depicts an initial screening of ten orphan heptahelix receptors using the screening method of Kotarsky et al. (Kotarsky et al., 2001) and linoleic acid (LA) as the ligand:
  A. HFF11 reporter cells each expressing a different orphan receptor (R1-R10) and control cell lines (HF1 and HFF11) stimulated with LA;
  B. Concentration response curves for LA and arachidonic acid (AA) using HFF11.pR10 and HFF11 cells; and
  C. Northern blot showing expression of FFAR (i.e. "Free Fatty Acid Receptor") (R10; GPR40) in different human organs of major physiological relevance and the murine pancreatic β-cell insulinoma cell line MIN-6.

In the initial screening, reporter cell lines, with or without recombinant test receptors, were challenged with FFAs, such as AA and LA, at 50 mM. Ten cell lines expressing ten "orphan receptors" (one receptor per cell line) were screened. The expressed receptors were labeled R1-R10. The cell line expressing the candidate receptor R10, (previously designated GPR40, Accession number AF024687 in GenBank (Sawzdargo, M. et al., 1997)) gave a strong and reproducible response to LA, with a Z-factor (Zhang, et al., 1999) of 0.8. (FIG. 1a.) M had no effect on R10 (FIG. 1b) or any other test receptor, R1-R9 (data not shown).

Northern blot analysis of select human tissues revealed that the corresponding gene for R10 is expressed mainly in the liver, heart, and the skeletal muscle. The receptor is also expressed in pancreatic β-cell insulinoma. (FIG. 1c.)

Figure 2:
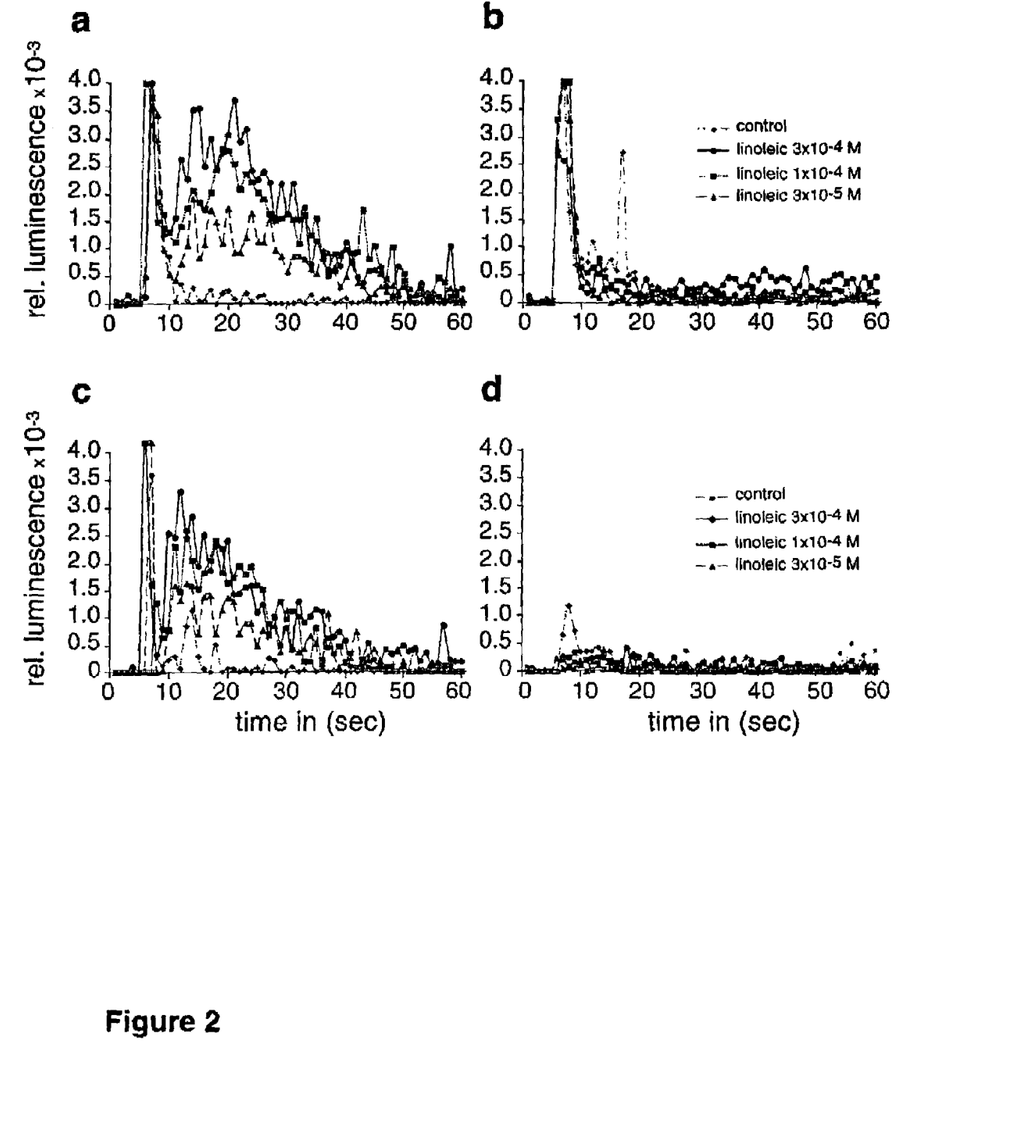
FIG. 2 depicts a time course of calcium release in CHO and HeLa cells transfected with a plasmid expressing the FFAR (R10; GPR40) receptor or a control plasmid, as assayed by luminescence of the $Ca^{2+}$ sensitive photoprotein aequorin, when stimulated with three different LA concentrations.

Activation of receptor R10 by LA was confirmed by stimulation in two different cell lines, CHO and HeLa, transiently co-transfected with expression vectors containing the R10 ORF (i.e., the gene encoding FFAR) and the calcium-activated photoprotein, aequorin. The results with this alternative reporter system showed that only cells transfected with the R10-encoding vector, in contrast to sham-transfected reporter cells, were capable of eliciting a calcium-mediated luminescence flash upon LA stimulation. (FIG. 2.)

Based on these results, it was concluded that R10 was activated by LA. In order to determine whether other FFAs could activate R10, and if so, what the structural requirements of the FFAs were to activate the receptor, the R10-expressing reporter cell line, HFF11.pR10, was subsequently exposed to a broad spectrum of FFAs (Table 1).

TABLE 1

FFAR response to a variety of active free fatty acids

| Trivial name | Chain length: Double bonds | Mean $EC_{50}$ (μM) | Systematic name |
|---|---|---|---|
| Capric acid | 10:0 | 12.6 | Decanoic acid |
| Lauric acid | 12:0 | 22.5 | Dodecanoic acid |
| Myristic acid | 14:0 | 30.3 | Tetradecanoic acid |
| Palmitic acid | 16:0 | 143.2 | Hexadecanoic acid |
| Oleic acid | 18:1 | 123.1 | cis-9-octadecanoic acid |
| Linoleic acid | 18:2 | 38.4 | cis-9, cis-12,-octadecanoic acid |
| Linoleic acid octadecanoic | 18:3 | 27.1 | cis-9, cis-12, cis-15- acid |
| γ-Linoleic acid octadecanoic | 18:3 | 28.5 | cis-6, cis-9, cis-12- acid |
| Stearidonic acid | 18:4 | 8.9 | cis-6, cis-9, cis-12-15- octadecanoic acid |
| CLA | 18:2 | 77.3 | trans-10, cis-12-octadecanoic acid |
| 9-HODE | 18:2 | 3.4 | (±)-9-hydroxy, trans-10, cis-12-octadecanoic acid |
| EDA | 20:2 | 20.0 | cis-11, cis-14- -eicosadienoic acid |
| Ricinoleic acid | 18:1 | 8.0 | 12-hydroxy, cis 9-octadecenoic acid |
| Ricinelaidic acid | 18:1 | 20.0 | 12-hydroxy, trans 9-octadecanoic acid |
| Elaidic acid | 18:1 | 120.0 | trans-9-octadecanoic acid |
| Hydroxystearic acid | 18:0 | 8 | 12-hydroxyoctadecanoic acid |
| Palmitoleic acid | 16:1 | 100 | hexadecenoic acid |
| Myristelaidic acid | 14:1 | 25 | trans-9-tetradecenoic acid |

The FFAs that were capable of activating this receptor include saturated as well as mono- and poly-unsaturated FFAs, all well within physiological concentration ranges. (Chung, et al.,1998). The receptor was activated by saturated FFAs comprising 10 to 18 carbon atoms. Medium-length saturated FFAs (10 to 12 carbon atoms) had the highest efficacies (order of potency: capric acid>lauric acid>myristic acid>palmitic acid). FFAs with chain lengths shorter than 10 carbon atoms were unable to activate the receptor at concentrations up to 1 mM (data not shown). The 18-carbon stearic acid was able to activate the receptor. However, due to its low solubility, a reliable $EC_{50}$ value could not be determined. Unsaturated FFAs with a chain-length shorter than 20 carbon atoms also activated the reporter cells, but with a lower efficacy (order of potency: stearidonic acid>linolenic acid>linoleic acid>oleic acid). In view of the broad spectrum of FFAs capable of activating R10, this receptor was named Free Fatty Acid Receptor, or FFAR.

Example 3

Activation of FFAR by Fatty Acid Derivatives

In addition to the essential FFAs, two substances of significant clinical interest were tested. 9-HODE (9-hydroxy,trans-10,cis-12-octadecanoic acid) is a hydroxy derivative of LA. It is a major component of oxo-LDL, associated with several aspects of arteriosclerosis. (Jira, et al., 1998). CLA (conjugated LA) is a group of LA derivatives, comprising two conjugated double bonds in different locations and chirality. They are dietary components with a spectrum of biological functions, including anticarcinogenic effects. (Pariza, et al., 2001.) Especially well studied is the 10-trans,12-cis CLA isomer which has been reported to increase fatty acid oxidation in 3T3 L1 preadipocytes and in HepG2 liver cells. (Pariza, et al., 2001.) As shown in Table 1, both 9-HODE and, to a lesser extent, 10-trans,12-cis CLA, activated FFAR.

The characteristics of tissue distribution of FFAR and the nature of the ligand spectrum prompted out investigation of certain pharmacologically active drugs, selected on the basis of their corresponding known tissue target patterns. In particular, the anti-obesity drug MEDICA 16, and the anti-diabetes drugs Rosiglitazone, Ciglitazone, Glibenclamide (glyburide), and Clofibrate were screened for their ability to interact with FFAR. MEDICA 16 (3,3,14,14-tetramethyl-hexadecanedioic acid) is an experimental drug that has been shown to exhibit antidiabetogenic and hypolipidemic actions in a rat model. (Russell, et al., 1998.) It has been reported to lower plasma levels of chylomicrons, triacylglycerols, and cholesterols. Its site of action is thought to be mainly liver, although drug actions have been recognized also in heart and pancreatic β-cells. (Russell, et al., 1995.) MEDICA 16 has also been described as a thyromimetic drug, increasing lipolysis. Thiazolidinediones (TZDs), also known as the "Glitazones", comprise a novel class of anti-diabetic drugs that have been shown to reduce plasma glucose levels and improve insulin sensitivity in adipose tissue, liver and muscle. (Willson, et al., 2000). Although their exact mechanism of action is unknown, reports indicate that the TZDs bind to and activate the nuclear receptor, PPARγ. (Lehmann, et al., 1995).

Figure 3:
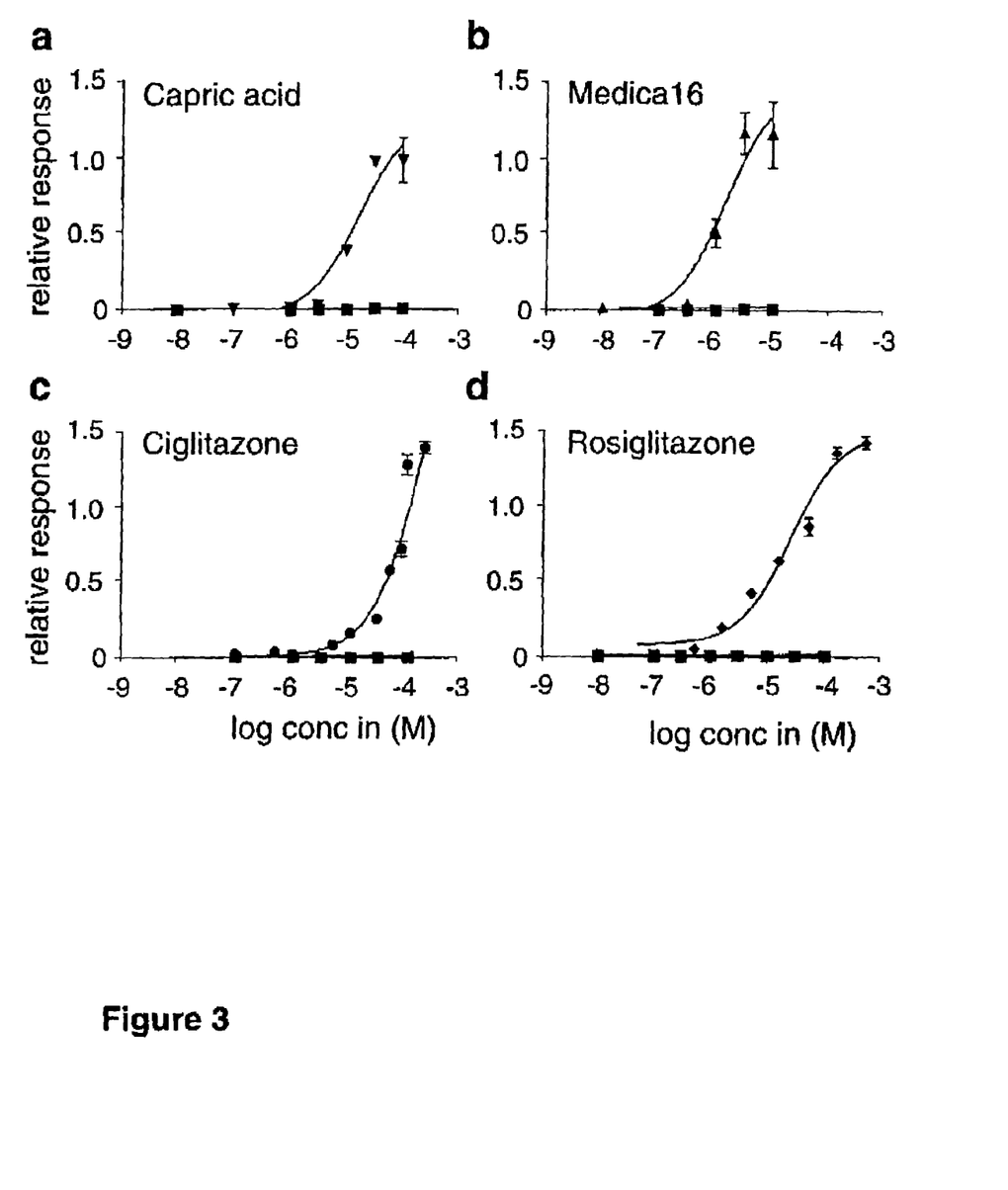
FIG. 3 depicts concentration response curves using HFF11 reporter cells expressing FFAR (R10; GPR40) in response to exposure to various compounds:
  A. The fatty acid capric acid ($EC_{50}$=12.6 µM);
  B. The anti-obesity drug MEDICA 16 ($EC_{50}$=1.22"0.1 µM);
  C. The anti-diabetic drug Ciglitazone ($EC_{50}$=84"3 µM); and
  D. the anti-diabetic drug Rosiglitazone ($EC_{50}$=3.8"0.8 µM).

Both the experimental anti-obesity drug, MEDICA 16 (Bar-Tana, et al., 1985) and the anti-diabetic thiazolidinediones Rosiglitazone (Cantello, et al., 1994) (SmithKline Beecham Pharmaceuticals) and Ciglitazone (Fujita, et al., 1983) strongly activated FFAR. (FIG. 3.) However, the non-thiazolidinedione type anti-diabetic drug, Glibenclamid (Tocris), and the non-thiazolidinedione type anti-hyperlipidemic drug Clofibrate (Tocris), were inactive (data not shown).

These observations are in accordance with recent reports of unexplained PPARγ-independent activity of TZDs. (Iwata, M. et al, 2001; Palakurthi, S. S., et al., 2001). Likewise, the presence of a surface receptor, like FFAR, conforms precisely with the direct and immediate effect of TZDs on skeletal muscle metabolism. (Brunmair, B., et al., 2001).

In summary, this invention identifies a cell surface receptor of the heptahelix receptor family, also known as the G-protein coupled receptor family and the seven-transmembrane receptor family, that is activated by a spectrum of FFAs of medium to long chain length at concentrations corresponding to their physiological plasma levels. The receptor is expressed in organs and tissues of major importance to fat and energy metabolism. This implies that it serves a role as a "nutrient sensor." It is activated by FFAs and structurally related, established anti-diabetic drugs, like the "glitazones." It is also activated by the anti-obesity drug MEDICA 16. Thus, the identification of this hitherto unrecognized receptor, FFAR, emphasizes the pivotal role of FFAs in an important physiological-pathological context, and provides a key to discovering new drugs that can be used to affect the metabolism of fatty acids and fatty acid derivatives, and thus treat diseases and disorders associated with the metabolism of fatty acids and fatty acid derivatives.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the following claims.

REFERENCES

All references cited in this application are hereby incorporated by reference in their entireties.

Ausubel, F. M., *Current Protocols in Molecular Biology*, Wiley, New York (1989).

Bar-Tana, J., Rose-Kahn, G. & Srebnik, M., "Inhibition of lipid synthesis by beta beta'-tetramethyl-substituted, C14-C22, alpha, omega-dicarboxylic acids in the rat in vivo", *J. Biol. Chem.* 260:8404-8410 (1985).

Berger, J. & Moller, D. E., "The mechanisms of action of PPARs", *Ann. Rev. Med.* 53:409-435 (2002).

Brunmair, B. et al., "Direct thiazolidinedione action on isolated rat skeletal muscle fuel handling is independent of peroxisome proliferator-activated receptor-gamma-mediated changes in gene expression", *Diabetes* 50:2309-2315 (2001).

Button, D. & Brownstein, M., "Aequorin-expressing mammalian cell lines used to report Ca2+ mobilization", *Cell Calcium* 14:663-671 (1993).

Cantello, B. C. et al., "[[omega-(Heterocyclylamino) alkoxy]benzyl]-2,4-thiazolidinediones as potent antihyperglycemic agents", *J. Med. Chem.* 37:3977-3985 (1994).

Chawla, A., Repa, J. J., Evans, R. M. & Mangelsdorf, D. J., "Nuclear receptors and lipid physiology: opening the X-files", *Science* 294:1866-1870 (2001).

Chung, B. H., Hennig, B., Cho, B. H. & Darnell, B. E., "Effect of the fat composition of a single meal on the composition and cytotoxic potencies of lipolytically-releasable free fatty acids in postprandial plasma", *Atherosclerosis* 141:321-332 (1998).

Fujita, T. et al., "Reduction of insulin resistance in obese and/or diabetic animals by 5-[4-(1 -methylcyclohexyl methoxy)benzyl]-thiazolidine-2,4-dione (ADD-3878, U-63,287, ciglitazone), a new anti-diabetic agent", *Diabetes* 32:804-810 (1983).

Funk, C. D., "Prostaglandins and leukotrienes: advances in eicosanoid biology", *Science* 294:1871-1875 (2001).

Iwata, M. et al, "Pioglitazone ameliorates tumor necrosis factor-alpha-induced insulin resistance by a mechanism independent of adipogenic activity of peroxisome proliferator-activated receptor-gamma", *Diabetes* 50:1083-1092 (2001).

Jira, W., Spiteller, G., Carson, W. & Schramm, A., "Strong increase in hydroxy fatty acids derived from linoleic acid in human low density lipoproteins of atherosclerotic patients", *Chem Phys Lipids* 91:1-11 (1998).

Kotarsky, K., Owman, C., and Olde, B. A., "Chimeric reporter gene allowing for clone selection and high-throughput screening of reporter cell lines expressing G-protein-coupled receptors", *Anal. Biochem.* 288:209-215 (2001).

Lehmann, J. M. et al., "An anti-diabetic thiazolidinedione is a high affinity ligand for peroxisome proliferator-activated receptor gamma (PPAR gamma)", *J. Biol. Chem.* 270:12953-12956 (1995).

Linder, M. C., (Editor) *Nutritional Biochemistry and Metabolism: With Clinical Applications*, Elsevier, New York (1991).

Louet, J. F. et al., "Long-chain fatty acids regulate liver carnitine palmitoyltransferase I gene (L-CPT I) expression through a peroxisome-proliferator-activated receptor alpha (PPAR alpha)-independent pathway", *Biochem J.* 354:189-197 (2001).

Massaro, M., et al. "Direct vascular antiatherogenic effects of oleic acid: a clue to the cardioprotective effects of the Mediterranean diet", *Cardiologia* 44(6):507-13 (June 1999).

Mastrangelo, A. M., et al., "Oleic Acid Increases Cell Surface Expression and Activity of CD11b on Human Neutrophils", *J. Immunol.* 161:4268-4275 (1998).

Nunez, E. A., "Biological complexity is under the <strange attraction' of non-esterified fatty acids", *Prostaglandins Leukot. Essent. Fatty Acids* 57:107-110 (1997).

Owman, C., Nilsson, C., and Lolait, S. J., "Cloning of cDNA encoding a putative chemoattractant receptor", *Genomics* 37:187-194 (1996).

Palakurthi, S. S., Aktas, H., Grubissich, L. M., Mortensen, R. M. & Halperin, J. A., "Anticancer effects of thiazolidinediones are independent of peroxisome proliferator-activated receptor gamma and mediated by inhibition of translation initiation:, *Cancer Res.* 61:6213-6218 (2001).

Pariza, M. W., Park, Y. & Cook, M. E., "The biologically active isomers of conjugated linoleic acid", *Prog. Lipid Res.* 40:283-298 (2001).

Russell, J. C. et al., "Development of insulin resistance in the JCR:LA-cp rat: role of triacylglycerols and effects of MEDICA 16", *Diabetes* 47:770-778 (1998).

Russell, J. C. et al., "Inhibition of atherosclerosis and myocardial lesions in the JCR:LA-cp rat by beta, beta'-tetramethylhexadecanedioic acid (MEDICA 16)", *Arterioscler. Thromb. Vasc. Biol.* 15:918-923 (1995).

Samuelsson, B., Hammarstrom, S., Hamberg, M. & Serhan, C. N., "Structural determination of leukotrienes and lipoxins", *Adv. Prostaglandin Thromboxane Leukot. Res.* 14:45-71 (1985).

Sauer, L. A., Dauchy, R. T. & Blask, D. E Mechanism for the antitumor and antiacachectic effects of n-3 fatty acids. *Cancer Res.* 60:5289-5295 (2000).

Sawzdargo, M. et al., "A cluster of our novel human G protein-coupled receptor genes occurring in close proximity to CD22 gene on chromosome 19q13.1", *Biochem. Biophys. Res. Commun.* 239:543-547 (1997).

Tryselius, Y., Nilsson, N. E., Kotarsky, K., Olde, B., and Owman, C., "Cloning and characterization of cDNA encoding a novel human leukotriene B(4) receptor", *Biochem. Biophys. Res. Commun.* 274:377-382 (2000).

Unger, R. H., "Lipotoxic diseases", *Ann. Rev. Med.* 53:319-336 (2002).

Willson, T. M., Brown, P. J., Sternback, D. D. & Henke, B. R., "The PPARs: from orphan receptors to drug discovery", *J. Med. Chem.* 43:527-550 (2000).

Zhang, J. H., Chung, T. D. & Oldenburg, K. R., "A Simple Statistical Parameter for Use in Evaluation and Validation of High Throughput Screening Assays", *J. Biomol. Screen.* 4:67-73 (1999).

APPENDIX

Human GPR40 (FAR1) nucleotide sequence:

[SEQ, ID NO.: 1]
ATGGACCTGCCCCCGCAGCTCTCCTTCGGCCTCTATGTGGCCGCCTTTGCG
CTGGGCTTCCCGCTCAACGTCCTGGCCATCCGAGGCGCGACGGCCCACGCC
CGGCTCCGTCTCACCCCTAGCCTGGTCTACGCCCTGAACCTGGGCTGCTCC
GACCTGCTGCTGACAGTCTCTCTGCCCCTGAAGGCGGTGGAGGCGCTAGCC
TCCGGGGCCTGGCCTCTGCCGGCCTCGCTGTGCCCCGTCTTCGCGGTGGCC
CACTTCTTCCCACTCTATGCCGGCGGGGCTTCCTGGCCGCCCTGAGTGCA
GGCCGCTACCTGGGAGCAGCCTTCCCCTTGGGCTACCAAGCCTTCCGGAGG
CCGTGCTATTCCTGGGGGGTGTGCGCGGCCATCTGGGCCCTCGTCCTGTGT
CACCTGGGTCTGGTCTTTGGGTTGGAGGCTCCAGGAGGCTGGCTGGACCAC
AGCAACACCTCCCTGGGCATCAACACACCGGTCAACGGCTCTCCGGTCTGC
CTGGAGGCCTGGGACCCGGCCTCTGCCGGCCCGGCCCGCTTCAGCCTCTCT
CTCCTGCTCTTTTTTCTGCCCTTGGCCATCACAGCCTTCTGCTACGTGGGC
TGCCTCCGGGCACTGGCCCGCTCCGGCCTGACGCACAGGCGGAAGCTGCGG
GCCGCCTGGGTGGCCGGCGGGCCCTCCTCACGCTGCTGCTCTGCGTAGGA
CCCTACAACGCCTCCAACGTGGCCAGCTTCCTGTACCCCAATCTAGGAGGC
TCCTGGCGGAAGCTGGGGCTCATCACGGGTGCCTGGAGTGTGGTGCTTAAT
CCGCTGGTGACCGGTTACTTGGGAAGGGGTCCTGGCCTGAAGACAGTGTGT
GCGGCAAGAACGCAAGGGGGCAAGTCCCAGAAGTAA

Human GPR40 (FAR1) peptide sequence:

[SEQ ID NO.: 2]
MDLPPQLSFGLYVAAFALGFPLNVLAIRGATAHARLRLTPSLVYALNLGCS
DLLLTVSLPLKAVEALASGAWPLPASLCPVFAVAHFFPLYAGGGFLAALSA
GRYLGAAFPLGYQAFRRPCYSWGVCAAIWALVLCHLGLVFGLEAPGGWLDH
SNTSLGINTPVNGSPVCLEAWDPASAGPARFSLSLLLFFLPLAITAFCYVG
CLRALARSGLTHRRKLRAAWVAGGALLTLLLCVGPYNASNVASFLYPNLGG
SWRKLGLITGAWSVVLNPLVTGYLGRGPGLKTVCAARTQGGKSQK

---

What is claimed is:

1. A method of screening for one or more compounds that affects an intracellular signal transduction pathway, said method comprising:
   a) contacting a cell that expresses a protein comprising the amino acid sequence of SEQ ID NO: 2 on its cell surface, and that comprises an intracellular signal transduction pathway that couples activation of the protein comprising the amino acid sequence of SEQ ID NO: 2 to expression of one or more reporter genes, with the one or more compounds under conditions where interaction of a compound with the protein comprising the amino acid sequence of SEQ ID NO: 2 can cause expression of the one or more reporter genes through one or more intracellular signal transduction pathways;
   b) measuring the level of activation of the protein comprising the amino acid sequence of SEQ ID NO: 2 by the one or more compounds by measuring expression of the one or more of the reporter genes;
   c) contacting a cell that expresses a protein comprising the amino acid sequence of SEQ ID NO: 2 on its cell surface, and that comprises an intracellular signal transduction pathway that couples activation of the protein comprising the amino acid sequence of SEQ ID NO: 2 to expression of one or more reporter genes, with rosiglitazone under conditions where interaction of a compound with the protein comprising the amino acid sequence of SEQ ID NO: 2 can cause expression of the one or more reporter genes through one or more intracellular signal transduction pathways;
   d) measuring the level of activation of the protein comprising the amino acid sequence of SEQ ID NO: 2 by rosiglitazone by measuring expression of the one or more of the reporter genes; and
   e) comparing the level of activation of the protein comprising the amino acid sequence of SEQ ID NO: 2 by the one or more compounds with the level of activation of the protein comprising the amino acid sequence of SEQ ID NO: 2 by rosiglitazone to thereby determine whether the one or more compounds affects the intracellular signal transduction pathway.

2. The method of claim 1, wherein the one or more compounds has a structure comprising
   a) a hydrophobic region comprising 10-18 carbon-carbon bonds, and
   b) a hydrophilic group on one or both ends of the hydrophobic region.

3. The method of claim 1, wherein the one or more compounds is a more potent activator of the protein comprising the amino acid sequence of SEQ ID NO: 2 than is rosiglitazone.

4. The method of claim 1, wherein the one or more compounds is a less potent activator of the protein comprising the amino acid sequence of SEQ ID NO: 2 than is rosiglitazone.

5. The method of claim 1, wherein the cell contacted with the one or more compounds is different than the cell contacted with rosiglitazone.

6. The method of claim 1, wherein the cell contacted with the one or more compounds is the same as the cell contacted with rosiglitazone.

7. The method of claim 1, further comprising measuring the baseline level of activation of the protein comprising the amino acid sequence of SEQ ID NO: 2 in the cell in the absence of the one or more compounds and rosiglitazone.

8. The method of claim 7, wherein the one or more compounds activates the protein comprising the amino acid sequence of SEQ ID NO: 2 to a higher than baseline level.

9. The method of claim 7, wherein the one or more compounds represses the protein comprising the amino acid sequence of SEQ ID NO: 2 activity to a lower than baseline level.

10. The method of claim 1, wherein the method is a high-throughput screening assay.

11. The method of claim 1, wherein the cell comprises a plasmid comprising the nucleotide sequence of SEQ ID NO: 1.

12. A composition comprising an isolated or purified protein comprising the amino acid sequence of SEQ ID NO: 2 bound to rosiglitazone.

* * * * *